United States Patent
Bransgrove

(10) Patent No.: US 8,894,950 B2
(45) Date of Patent: Nov. 25, 2014

(54) SEALING MEANS FOR TEST CASSETTE

(71) Applicant: Brandon Bransgrove, Gordon (AU)

(72) Inventor: Brandon Bransgrove, Gordon (AU)

( * ) Notice: Subject to any disclaimer, the term of this patent is extended or adjusted under 35 U.S.C. 154(b) by 0 days.

(21) Appl. No.: 13/882,468

(22) PCT Filed: Sep. 17, 2012

(86) PCT No.: PCT/AU2012/001116
§ 371 (c)(1),
(2), (4) Date: Apr. 29, 2013

(87) PCT Pub. No.: WO2013/040630
PCT Pub. Date: Mar. 28, 2013

(65) Prior Publication Data
US 2014/0054190 A1 Feb. 27, 2014

(30) Foreign Application Priority Data
Sep. 21, 2011 (AU) ............................... 2011903884

(51) Int. Cl.
*A61J 1/06* (2006.01)
*B65D 85/67* (2006.01)
*G01N 27/327* (2006.01)
*G01N 33/487* (2006.01)

(52) U.S. Cl.
CPC ............ *B65D 85/67* (2013.01); *G01N 27/3272* (2013.01); *G01N 33/48764* (2013.01); *G01N 33/48778* (2013.01); *B65H 2701/37* (2013.01)
USPC .......................................... 422/554; 422/560

(58) Field of Classification Search
USPC .............. 422/63, 66, 402, 403, 430, 554, 560
See application file for complete search history.

(56) References Cited

U.S. PATENT DOCUMENTS

| | | | |
|---|---|---|---|
| 4,218,421 A | 8/1980 | Mach, Jr. et al. | |
| 5,077,010 A | 12/1991 | Ishizaka et al. | |
| 5,120,506 A | 6/1992 | Saito et al. | |
| 2007/0065340 A1 | 3/2007 | Sacherer | |
| 2008/0286149 A1 | 11/2008 | Roe et al. | |
| 2009/0098644 A1 | 4/2009 | Sacherer et al. | |

FOREIGN PATENT DOCUMENTS

WO   WO2004/056269 A1   7/2004

OTHER PUBLICATIONS

International Search Report and Written Opinion of PCT/AU2012/001116 mailed on Nov. 21, 2012, 12 pages.

*Primary Examiner* — Jill Warden
*Assistant Examiner* — Dwayne K Handy
(74) *Attorney, Agent, or Firm* — Kilpatrick Townsend & Stockton LLP

(57) ABSTRACT

Disclosed is a test cassette comprising a continuous length of test carrier tape (22) in a supply chamber (12), the supply chamber (12) having an opening (52) sized so as to allow the test carrier tape (22) to pass through into a test zone (32) into an uptake chamber (14) where the test carrier tape (22) coils itself onto an uptake mandrel (26), the supply chamber (12) being sealed from the environment whereby the opening (52) of the supply chamber (12) allowing the exit of the test carrier tape (22) has a spacer (42) disposed either side of it, filling the remaining width of the opening (52) of the housing (16), a cover plate (34) being biased by a spring (38) to cover the spacer (42) and tape (22), thus covering the opening (52) and sealing the cassette (10).

20 Claims, 4 Drawing Sheets

SEALING MEANS FOR TEST CASSETTE

TECHNICAL FIELD

The present invention relates to fluid testing devices and, more specifically, to fluid testing devices configured as test cassettes.

BACKGROUND ART

It is known in the relevant art to analyze body fluid samples such as, for example, blood, plasma, urine, and interstitial fluid, may be analyzed for various components or properties. Such components or properties may include, for example, glucose, cholesterol, pathogens, drugs of abuse, coagulation, and haematocrit. In a typical test procedure, the body fluid sample is applied to a test zone containing one or more reactive ingredients. A reaction occurs in the test zone, and an analysis result is produced. An instrument may be used to read the analysis result, or the analysis result can be interpreted by eye using, for example, colour matching or symbols such as bars and/or dots.

A plurality of test zones may be supplied as a linear array of individual test zones along a carrier tape. The carrier tape may be disposed in a housing to form a unit known as a "test cassette." In a typical configuration, the test cassette may comprise two chambers, one chamber containing unused test material and the other chamber containing used test material. Test cassettes are known for use in laboratory analysers, as well as in portable analysers.

U.S. Pat. No. 4,218,421 issued to Mack et al., discloses a carrier tape with spacings between test zones, the carrier tape housed in a test cassette that has a storage chamber for unused test zones and a storage chamber for used test zones. A barrier means isolates the two storage chambers. U.S. Pat. No. 5,077,010 issued to Ishizaka et al. discloses a cassette housing transparent carrier tape with information fields and test fields. Test fields are read optically from the underside of the tape. Ishizaka '010 also teaches that the motor used to advance the tape, sufficient for a single test, can be guided by marks made along the tape at intervals. These marks can be read by a photoelectric switch. One or more flexible gaskets may be used to keep humidity out of the unused test zone chamber. However, the flexible gasket seal is able to preserve the unused tests for only a few days.

U.S. Pat. No. 7,582,258B2 issued to Ruhl et al. describes a test cassette with separate test zone chambers for the unused carrier tape and the used carrier tape, with a hydraulic sealing means used to prevent moisture entering the unused carrier tape chamber. The sealing means is pressurized by downward pressure applied by a stamp, causing the sealing means to press directly onto the carrier tape and to thus seal the carrier tape against the test cassette. Ruhl '258 also describes a gasket similar to that taught by Ishizaka '010, but utilizes two gaskets inclined in opposite directions to one another. In all embodiments, a deformable gasket is pressed directly onto the carrier tape.

In the above examples of the prior art, a sealing means employed presses a flexible gasket directly onto a carrier tape and creates a drag on the carrier tape as the carrier tape moves through the flexible gasket. Alternatively, the gasket seal may be broken by opening the gasket seal as the carrier tape is advanced, but in so doing the unused test material may be exposed to humidity.

DISCLOSURE OF THE INVENTION

Disclosed is an effective moisture seal assembly suitable for use in a test cassette. The moisture seal assembly, which does not require a flexible gasket, can be provided by pressing the test cassette carrier tape between two flat surfaces, and filling any gap on either side of the carrier tape with an adhesive, or with a spacer configured to occupy the gap. The cassette housing provides one of the two flat surfaces. It can be appreciated that the amount of moisture moving between the flat surfaces and the carrier tape can be minimized by applying moderate pressure to a cover plate contacting the carrier tape, as the carrier tape with unused test zones is guided out of the supply chamber. This seal assembly configuration has the advantage of producing less drag on the carrier tape and test zones, compared to conventional configurations, when the carrier tape is advanced. This reduces the amount of force needed to advance the carrier tape.

In one aspect of the present invention, a test cassette comprises: a cassette housing for enclosing a specified length of a carrier tape in a supply chamber, the supply chamber having an opening sized so as to allow carrier tape test zones to pass therethrough; and a seal assembly, the seal assembly including a spacer disposed against a surface of the cassette housing proximate the supply chamber opening.

In another aspect of the present invention, a seal assembly comprises: a spacer disposed against a surface of a housing of a test cassette proximate an opening in a supply chamber; a cover plate disposed adjacent the spacer, the cover plate attachable to the surface of the housing of the test cassette; and a spring disposed such that, when attached to the cover plate, the spring exerts a force on the spacer to provide a moisture barrier at the supply chamber opening.

In still another aspect of the present invention, a method for providing a moisture barrier for a test cassette comprises the steps of: placing a spacer on a surface of the test cassette; attaching a cover plate so as to secure the spacer to the surface of the test cassette; and securing a spring onto the cover plate.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures, in which.

MODES FOR CARRYING OUT THE INVENTION

Figure 1:
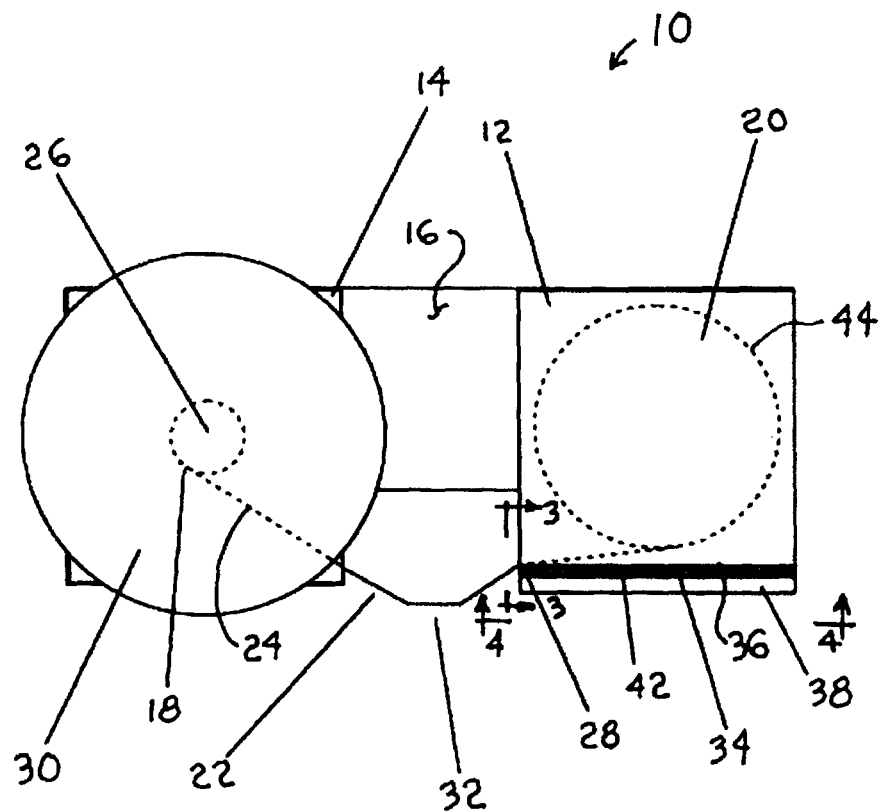
FIG. 1 is a simplified top view diagram of an exemplary embodiment of a test cassette comprising a cover plate positioned against the test cassette housing surface and held in place by a spring, to provide a seal assembly, in accordance with an aspect of the present invention.
Figure 2:
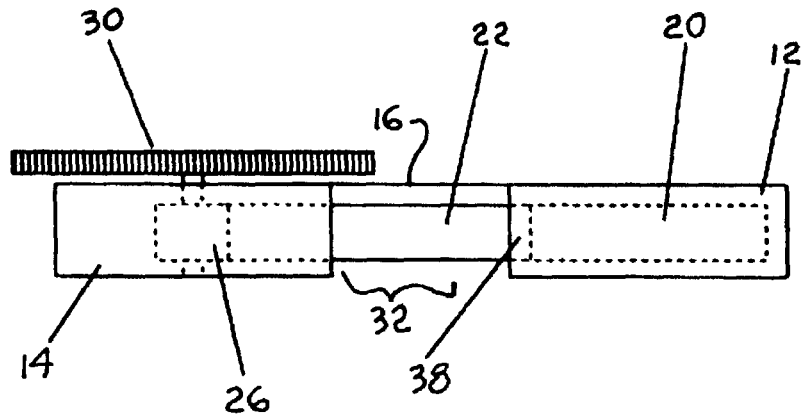
FIG. 2 is a simplified front view diagram of the test cassette of FIG. 1, showing a carrier tape visible in an analysis zone.

There is shown in FIGS. 1 and 2, simplified diagrams of an exemplary embodiment of a test cassette 10, in accordance with the present invention. The test cassette 10 comprises a supply chamber 12, an uptake chamber 14, and a cassette housing 16 supporting both the supply chamber 12 and the uptake chamber 14. The supply chamber 12 encloses a specified length of carrier tape 22 wound into a coiled supply roll 20. As shown in FIG. 1, a leading end 24 of the carrier tape 22 may be attached to an uptake mandrel 26 disposed within the uptake chamber 14. The cassette housing 16 may be fabricated by injection moulding using a plastic, a polymer, a thermoplastic elastomer, or polypropylene, for example.

A drive wheel 30 may be attached to the uptake mandrel 26 such that, when the drive wheel 30 is rotated, the uptake mandrel 26 is likewise rotated, causing a length of carrier tape 22 to: (i) be pulled out of the supply chamber 12, (ii) exit the supply chamber 12 via a supply chamber opening 28, (iii) be exposed for tests in an analysis zone 32, and (iii) be coiled onto the uptake mandrel 26. As shown in the illustration, the analysis zone 32 is defined by a carrier tape path between the supply chamber 12 and the uptake chamber 14 where a portion of the carrier tape 22 is exposed to allow access to successive unused test zones.

Figure 3:
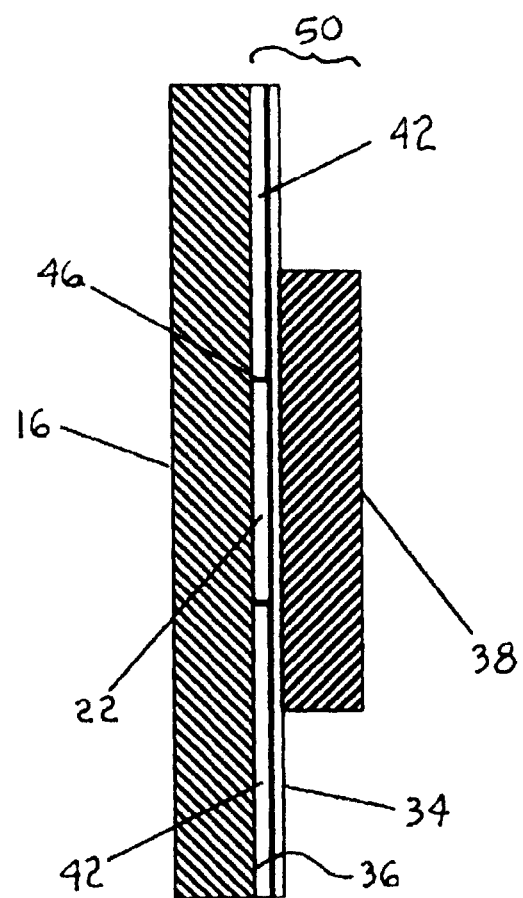
FIG. 3 is a sectional view of the test cassette of FIG. 1 showing a spacer positioned between the cover plate and the test cassette housing surface.
Figure 4:
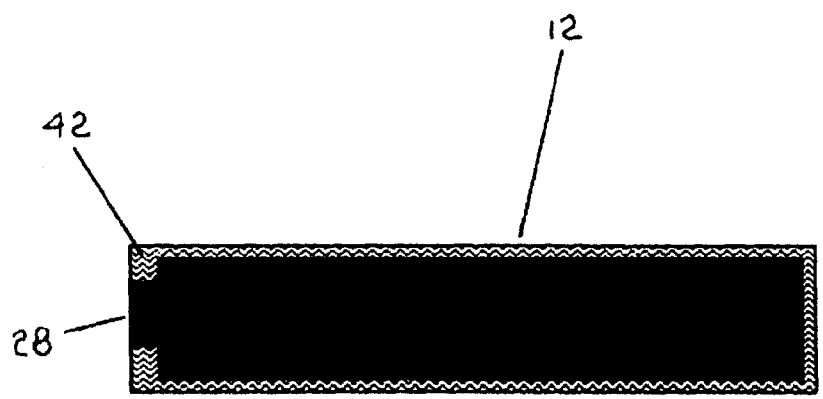
FIG. 4 is a sectional view of the test cassette of FIG. 1 showing the spacer positioned on a supply chamber.

A cover plate 34 may be positioned against a cassette housing surface 36 and held in place by a spring 38 such that, as the carrier tape 22 passes through the supply chamber opening 28, the cover plate 34 exerts a specified force on the carrier tape 22, as can be seen in greater detail in FIG. 3. Preferably, the cover plate 34 functions to provide an effective light and moisture barrier between the supply chamber 12 and ambient air. A drying agent (not shown) may also be disposed in the supply chamber 12 to take up any moisture that may have migrated into the supply chamber 12 from the ambient air. FIG. 4 shows the supply chamber 12 without the cover plate 34 or the spring 38 in place. The carrier tape 22 (not shown) exits from supply chamber opening 28 when the test cassette 10 is in use. As can be seen, the supply chamber opening 28 is defined by the cassette housing surface 36, and is bordered by the spacer 42.

In an exemplary embodiment, the cover plate 34 may comprise aluminum foil, as this can provide an excellent moisture and light barrier at low cost. In an exemplary embodiment, the cover plate 34 may be fabricated from aluminum foil having a thickness of approximately 80 microns. The aluminum foil can include a layer or coating on one or both sides such as, for example, polypropylene which can be used to heat seal the cover plate foil to the cassette housing surface 36. Alternatively, a material such as polyethylene terephthalate (PET) or acrylonitrile butadienestyrene (ABS) can be used in place of aluminum. However, use of such non-metallic materials may require a greater thickness than 80 microns so as to provide the desired moisture and light barrier.

As shown in FIG. 3, a spacer 42 is disposed between the cover plate 34 and the cassette housing 16. The spacer 42 performs two functions: (i) the thickness of the spacer 42 is approximately the same as the thickness of the carrier tape 22 so as to limit the force that can be applied to the carrier tape 22 by the cover plate 34 and (ii) use of the spacer 42 can close a void, such as a gap 46, that might otherwise be present between the cover plate 34 and the cassette housing surface 36, where an open void can allow moisture to enter the supply chamber 12. The spacer 42 may be fabricated from a flexible material so as to relax tolerance requirements on the thickness of the spacer 42. In an exemplary embodiment, the spacer 42 may comprise a double sided adhesive tape material, a layer of adhesive material, foam material, or rubber material, for example. Alternatively, the spacer 42 may be co-moulded and integral with the cassette housing 16.

The spring 38 may comprise metal, plastic, or rubber having a thickness and modulus of elasticity appropriate to supply a sufficient force to keep the carrier tape 22 pressed against the cassette housing 16. The spring 38 also applies pressure to the spacer 42 such that the spacer 42 expands slightly towards the edges of the carrier tape 22 and serves to reduce the size of any voids. As can be appreciated by one skilled in the art, the spring 38 exerts an inward force against the cover plate 34 such that, as the carrier tape 22 passes through the supply chamber opening 28, the cover plate 34 in turn exerts a force on the carrier tape 22. A seal assembly 50 thus comprises the spacer 42, the cover plate 34, and the spring 38.

The carrier tape 22 may support a plurality of test zones (not shown) spaced at intervals along a specified length of the carrier tape 22. A fluid sample may be applied to a test zone exposed in the analysis zone 32, and a result produced, as is well known in the art. In the case of a photochemical test, the carrier tape 22 may be comprised of a transparent substrate, and the colour produced may be read from the underside of the carrier tape 22. If the detection method is electrochemical, the carrier tape 22 need not be transparent.

There are numerous detection methods known to those skilled in the art and the characteristics of the carrier tape 22 can be tailored to the particular method to be used in analysis. The thickness of the carrier tape 22 can vary. In an exemplary embodiment, the thickness can range from about 5 microns to over 100 microns. Thinner carrier tapes 22 can be used where a smaller volume is desired for the supply chamber 12. Using a thinner carrier tape 22 can allow for a smaller and less expensive test cassette 10, or provide for a larger numbers of test zones in the test cassette 10.

The width of the carrier tape 22 may be specified to accommodate the size of the test zone or, in the case of multiple parameters, the different sizes of all the test zone widths. As the width of the carrier tape 22 is increased, so too does the size of the seal assembly 50 comprising the spacer 42, the cover plate 34, and the spring 38. In the case of a relatively wide seal assembly 50, it may be necessary to use a relatively flexible cover plate 34 in order to ensure tight mating of the surfaces of the spacer 42 and the cover plate 34. A flexible top cover plate 22 will thus function to ensure the carrier tape 22 is pressed substantially flat onto the cassette housing 16, even if there is slight unevenness in the thickness of the carrier tape 22 or on the surface of the cassette housing 16.

Preferably, the flexible surface is specified so as to ensure minimum drag when the carrier tape 22 is advanced so as to pass through the seal assembly 50. It may be possible to use aluminum foil pressed onto substantially the entire length of the carrier tape 22 by a relatively flexible spring surface, such as rubber for example. In all embodiments, the portion of the carrier tape 22 is pressed between the surface of the cassette housing 16 and a substantially flat cover plate 34 that does not "grab" or grip the carrier tape 22 as the carrier tape 22 is guided through the supply chamber opening 28.

After the testing has been completed, the carrier tape 22 may be advanced to store used test zones 18 in the uptake chamber 14. The carrier tape 22 may be advanced by manually turning the drive wheel 30. However the drive wheel 30 can be motorised, mechanized, or in some other way automated (not shown). The uptake chamber 14 does not require a corresponding seal assembly as there is no need to regulate the ambient humidity for used test zones 18. The uptake chamber 14 serves primarily as a convenient place for storage of used carrier tape 22.

Spacing between test zones is specified so as to ensure that a following, unused test zone 44 remains in the sealed supply chamber 12 as a current, used test zone 18 is entering the uptake chamber 14. Accordingly, after testing, the section of carrier tape 22 disposed between the supply chamber 12 and the uptake chamber 14 is exposed to ambient humidity. The seal assembly 50 essentially defines a plane of demarcation such that an unused test zone 44 remains on one side of the seal assembly 50 and inside the supply chamber 12, and used test zones 18 are disposed on the other side of the seal assembly 50. Each time a test zone is moved through the supply chamber opening 28, the cover plate 34 moves to allow for passing of the extra thickness of the unused test zone 44. The cover plate 34 repositions after the unused test zone 44 has cleared the supply chamber opening 28. This movement of the cover plate 34 is allowed by the spring 38 which holds the cover plate 34 in position over the carrier tape 22.

Figure 5:
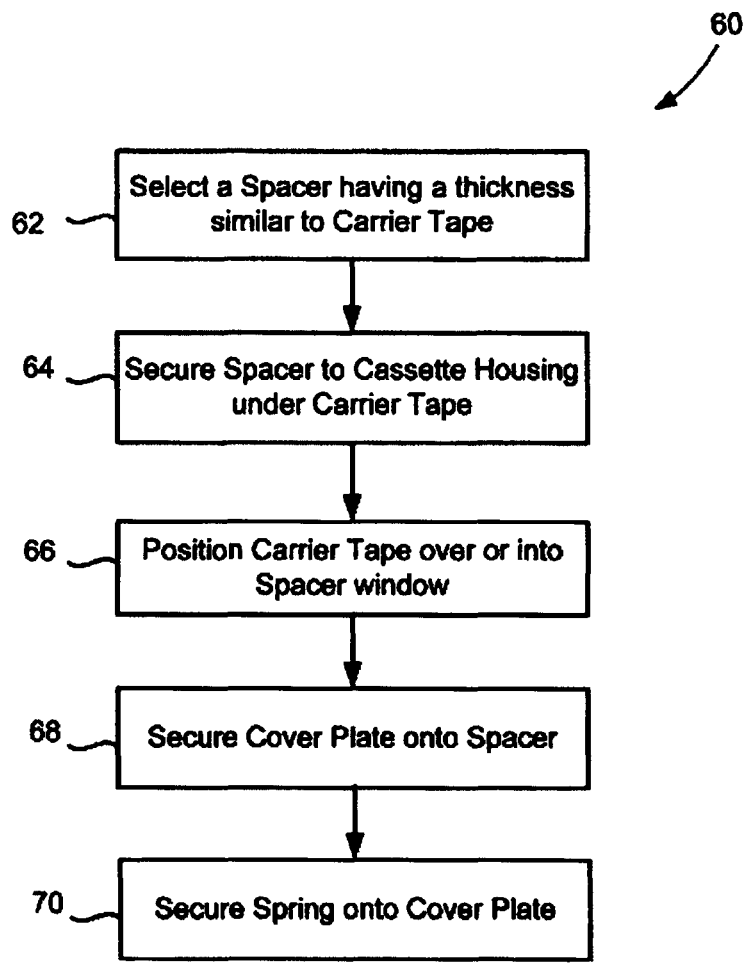
FIG. 5 is a flow diagram illustrating emplacement of a housing seal onto the test cassette of FIG. 1.

Emplacement of the seal assembly 50 onto a test cassette can be described with reference to a flow diagram 60 in FIG. 5. As shown in FIG. 5, a user selects a compatible spacer 42 for attachment to the housing of the test cassette, at step 62. The spacer 42 is secured to the test cassette housing after placement under the carrier tape 22, at step 64. The width of the spacer window 52 is substantially the same as the width of the carrier tape 22. Accordingly, when the spacer 42 is placed under the carrier tape 22, the spacer 42 is positioned so that the carrier tape 22 either overlaps the spacer window 52, or fits inside the spacer window 52, at step 66.

Figure 6:
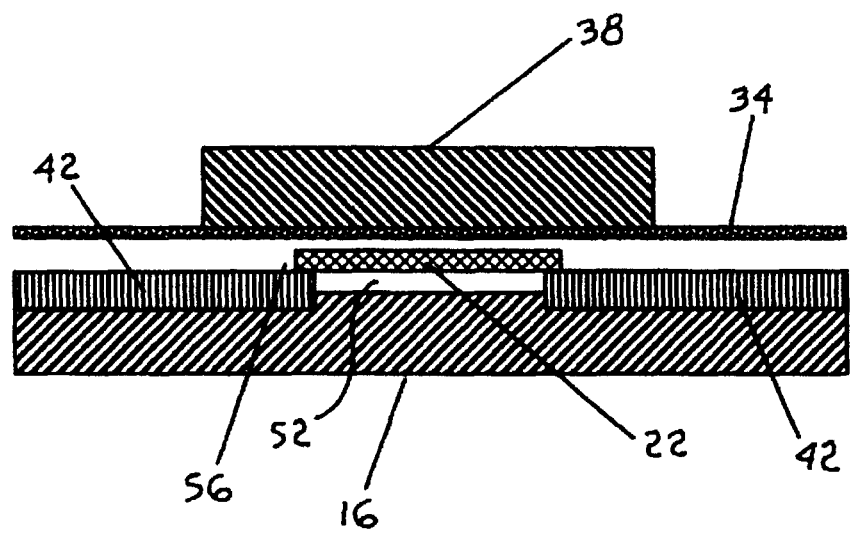
FIG. 6 is a sectional view of the test cassette of FIG. 1 showing the seal assembly prior to the attachment of the cover plate to the test cassette housing; and, FIG. 7 is a sectional view of the test cassette of FIG. 1 showing the seal assembly after the attachment of the cover plate to the test cassette housing.
Figure 7:
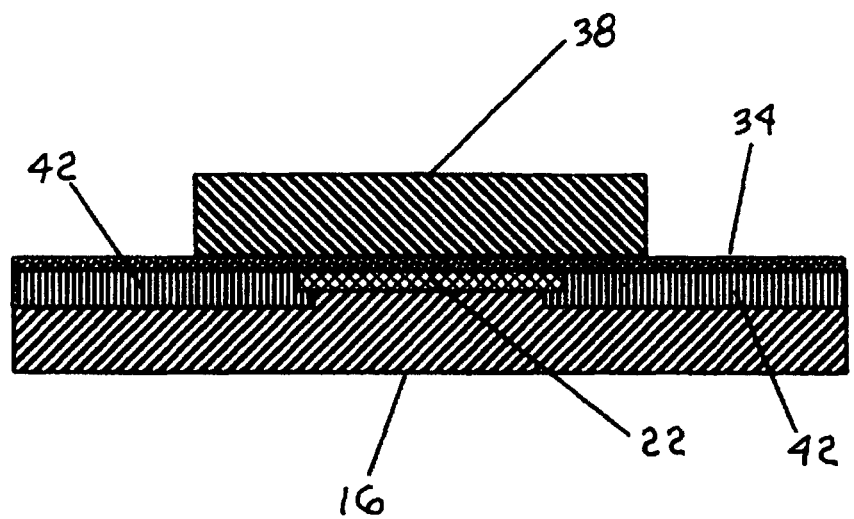

As shown in the exemplary embodiment of FIG. 3, the carrier tape 22 fits into the spacer window 52, and serves to minimize the size of any gap 54 that may be present, whereas in the exemplary embodiment of FIG. 6, the width of the carrier tape 22 is slightly greater than the width of the spacer window 52. The cover plate 34 is secured over the carrier tape 22 and the spacer 42, at step 68, and serves to minimize the size of any gap 56 that may be present. Finally, at step 70, the spring 38 is secured to the cover plate 34, as shown in FIG. 7.

It can be appreciated by one skilled in the relevant art that advantages of the present invention include, without limitation, a seal assembly which reduces the friction or drag on a test cassette carrier tape that, in the prior art, has been associated with gaskets to isolate test zones from humid air. Specifically, the disclosed seal assembly utilizes two flat surfaces that are attached to the test cassette housing, and do not attempt to deform around the carrier tape which is placed on a spacer window. Critically, the space on either side of the carrier tape may be filled by separate spacers that are essentially the same thickness as the carrier tape, and may be urged against the sides of the carrier tape when pressed by a cover plate.

The disclosed seal assembly is readily adaptable to various thicknesses of carrier tape by using spacers that match the thickness of the carrier tape. As the flat surfaces above and below the carrier tape do not need to deform around the sides of the carrier tape, there is no need for the two surfaces to comprise rubber or a similar gripping material having low Shore hardness. The embodiments disclosed herein show that a metal foil such as aluminum, or a plastic such as ABS, may be used for the cover plate and the test cassette housing. Such materials allow carrier tape, commonly made from PET or polycarbonate, to slide rather than to grip. The disclosed low friction seal assembly thus has the advantage of reducing the force required to advance a carrier tape, a feature which can increase the battery life of motorized test cassette devices, or may simply improve ease of use for a manually-operated test cassette device.

INDUSTRIAL APPLICABILITY

The disclosed test cassette seal assembly configuration provides for a moisture seal that does not require a flexible gasket. The test cassette carrier tape is routed between two flat surfaces, and any gap present at the carrier tape may be filled with an adhesive or with a spacer configured to occupy the gap. The amount of moisture entering the test cassette is minimized by the application of spring pressure to a cover plate contacting the carrier tape as the carrier tape is guided out of a chamber. This seal configuration has the advantage of decreasing drag on the carrier tape, and reducing the amount of force needed to advance the carrier tape.

What is claimed is:

1. A test cassette including:
   a housing with a supply chamber for carrying a length of carrier tape, the housing having a right side wall, a left side wall and an opening where the carrier tape exits the supply chamber for testing, wherein the opening is positioned between the right side wall and the left side wall; and
   a seal assembly for restricting moisture entering the supply chamber as the carrier tape is removed through the opening, wherein the seal assembly includes:
   a cover plate attached relative to the housing to press and seal against the tape adjacent the opening;
   a spacer positioned between the cover plate and the housing, wherein the spacer is of substantially the same thickness as the carrier tape and includes a left portion near the left side wall and a right portion near the right side wall that defines an open window under the cover plate between the left portion and the right portion to accommodate the tape when the cover plate presses against the tape and spacer, as the tape is drawn through the seal assembly to exit the opening in the supply chamber; and
   a biasing member to urge the cover plate against the carrier tape.

2. The test cassette of claim 1, wherein the housing provides a flat surface against which the tape is pressed by the cover plate as the tape is drawn through the window.

3. The test cassette of claim 2, wherein the housing and the cover plate both define flat surfaces for the tape to seal against as the tape passes between the housing and cover plate.

4. The test cassette of claim 1, wherein the window of the spacer is designed to accommodate the tape so that edges of the tape fit within the window so as to substantially fit between the right portion and the left portion.

5. The test cassette of claim 4, wherein the spacer is formed of flexible material so as to expand toward and seal against the edges of the tape when the cover plate presses against the spacer and tape.

6. The test cassette of claim 1, wherein the window of the spacer is designed to be of a reduced dimension relative to the tape so that the tape sits between the spacer and the cover plate, and wherein the spacer is flexible so that the edges of the tape embed in the spacer when the cover plate presses against the tape.

7. The test cassette of claim 1, wherein the cover plate is adapted to flex in order to accommodate variation in thickness of the tape.

8. The test cassette of claim 7, wherein the cover plate is integrally formed with the housing.

9. The test cassette of claim 1, wherein the spacer comprises at least one of a double sided adhesive material, a layer of adhesive material, foam material and rubber material.

10. The test cassette of claim 1, wherein the spacer is integrally molded with the housing.

11. The test cassette of claim 1, wherein the cover plate comprises polypropylene.

12. The test cassette of claim 1, wherein the biasing member is a spring comprised of at least one of metal, plastic and rubber.

13. The test cassette of claim 1, further comprising an uptake chamber enclosing an uptake mandrel, the uptake mandrel being configured to receive the carrier tape from the supply chamber.

14. The test cassette of claim 12, wherein the supply chamber is spaced apart from the uptake chamber so as to form an analysis zone there between, wherein a portion of the carrier tape is exposed in the analysis zone for testing.

15. A seal assembly for sealing around a carrier tape as it exits an opening in a supply chamber of a test cassette, including:
 a cover plate attached in a biased manner relative to a housing of the supply chamber, to press and seal against the tape adjacent the opening that is defined by a right side wall and a left side wall; and
 a spacer positioned between the cover plate and the housing so as to fit between the right side wall and the left side wall, wherein the spacer is of substantially the same thickness as the carrier tape and defines a window under the cover plate to accommodate the tape when the cover plate presses against the tape and spacer, as the tape is drawn through the seal assembly to exit the opening in the supply chamber; and a biasing member to urge the cover plate against the carrier tape.

16. The seal assembly of claim 15, wherein the cover plate also has a flat surface that presses and seals against the tape as the tape passes between the flat surface of the housing and flat surface of the cover plate.

17. The seal assembly of claims 15, wherein the biasing member is a spring comprised of at least one of metal, plastic and rubber.

18. The seal assembly of claim 15, wherein the spacer is formed of flexile material to accommodate and seal with edges of the tape when the cover plate is pressed against the spacer.

19. The seal assembly of claim 15, wherein the cover plate is adapted to flex in order to accommodate variation in thickness of the tape.

20. A method of providing a moisture barrier for a carrier tape exiting an opening in a supply chamber of a test cassette as claimed in claim 1, including:
 placing the spacer on a surface of the supply chamber housing;
 attaching the cover plate so as to secure the spacer to the surface of the housing, whereby to seal against the carrier tape as the carrier tape passes between the surface and the cover plate; and, securing a biasing member to the cover plate to urge the cover plate toward the spacer.

* * * * *